United States Patent
Strahle

(10) Patent No.: US 6,598,972 B2
(45) Date of Patent: Jul. 29, 2003

(54) STEREOMICROSCOPY SYSTEM

(75) Inventor: Fritz Strahle, Heubach (DE)

(73) Assignee: Carl Zeiss-Stiftung (DE)

(*) Notice: Subject to any disclaimer, the term of this patent is extended or adjusted under 35 U.S.C. 154(b) by 56 days.

(21) Appl. No.: 09/964,251

(22) Filed: Sep. 26, 2001

(65) Prior Publication Data
US 2002/0075449 A1 Jun. 20, 2002

(30) Foreign Application Priority Data
Sep. 26, 2000 (DE) .......................... 100 47 617

(51) Int. Cl.$^7$ ................................................ A61B 3/10
(52) U.S. Cl. ....................................................... 351/216
(58) Field of Search ........................ 351/205, 206, 351/214, 216, 245; 359/372, 373, 374, 376, 388, 831, 834, 835

(56) References Cited

U.S. PATENT DOCUMENTS

| | | | |
|---|---|---|---|
| 4,710,000 A | 12/1987 | Spitznas et al. ............ | 350/516 |
| 4,723,842 A | 2/1988 | Twisselmann et al. ...... | 350/511 |
| 4,728,183 A | 3/1988 | Heacock et al. ............ | 351/219 |
| 4,991,947 A | 2/1991 | Sander et al. ............... | 350/507 |
| 5,009,487 A | 4/1991 | Reiner ......................... | 350/286 |
| 5,200,773 A | 4/1993 | Volk ............................ | 351/219 |
| 5,302,988 A | 4/1994 | Nanjo ......................... | 354/62 |
| 5,321,447 A | 6/1994 | Sander et al. ............... | 351/216 |
| 5,535,060 A | 7/1996 | Grinblat ...................... | 359/835 |
| 5,986,801 A | 11/1999 | Volk et al. ................... | 359/376 |
| 6,076,929 A | 6/2000 | Stuttler ........................ | 351/211 |
| 6,212,006 B1 | 4/2001 | Reiner ......................... | 359/388 |
| 6,474,815 B1 * | 11/2002 | Ulbers et al. ................ | 351/214 |

FOREIGN PATENT DOCUMENTS

| | | | |
|---|---|---|---|
| DE | 3507 458 A1 | 9/1986 | |
| DE | 35 39 009 A1 | 5/1987 | |
| DE | 36 15842 A1 | 11/1987 | |
| DE | 38 26 069 C2 | 2/1990 | |
| DE | 41 14 646 A1 | 11/1992 | |
| DE | 94 15 219.5 | 1/1995 | |
| DE | 299 05 969 U1 | 8/1999 | |
| DE | 200 21 955 U1 | 4/2001 | |
| EP | 0 193 818 A1 | 9/1986 | |
| EP | 0 701 706 B1 | 3/1996 | |
| ES | 2 116 933 | 7/1998 | ............ G02B/5/04 |

OTHER PUBLICATIONS

European Search Report, Dated Apr. 12, 2002 4 pages.
Translation of German Utility Model DE 200 21 955 U1, Publication Date Apr. 19, 2001, 17 pages.
Summary of German Utility Model G94 15 219.5 U1, Publication Date Jan. 12, 1995, 1 page.
English translation of DE 35 39 009 A1, Publication Date May 7, 1987, 10 pages.
European Search Report dated Jan. 23, 2003 (1 page).

* cited by examiner

Primary Examiner—George Manuel
(74) Attorney, Agent, or Firm—Rosenthal & Osha L.L.P.

(57) ABSTRACT

A stereomicroscopy system is disclosed for viewing an object and/or an intermediate image produced of an object, in microsurgery. The stereomicroscopy system includes an objective system with an object plane for positioning the object and/or the intermediate image to be viewed. The stereomicroscopy system also includes a beam interchanging and image inverting system. The beam interchanging and image inverting system supplies a first beam bundle directed to the left from the object plane in the direction of the objective system to the right of the objective system. The beam interchanging and image inverting system also supplies a second beam bundle directed to the right from the object plane in the direction of the objective system to the left of the objective system. The beam interchanging and image inverting system also inverts image orientations of the two beam bundles. The beam interchanging and image inverting system includes at least one Porro prism of the second kind.

22 Claims, 10 Drawing Sheets

STEREOMICROSCOPY SYSTEM

BACKGROUND OF INVENTION

1. Field of the Invention

The invention relates generally to a stereomicroscopy system for viewing an object or an intermediate image produced of an object. This intermediate image may be a vertically and horizontally inverted image of an object, and the microscopy system may be utilized in microsurgery, in particular, for carrying out eye surgeries.

2. Background Art

Stereomicroscopes are known in the art. FIG. 11 schematically depicts a beam path of a conventional stereomicroscope. In the conventional stereomicroscope, the viewer looks with his two eyes 901 and 902 into a left ocular 903 and a right ocular 904, respectively, and views, for example, an object positioned in an object plane 905 of the microscope. The oculars 903 and 904 together with image inverting prisms 915 and tube lenses 913 form the tube which functions as a binocular Keplerian telescope. The object is perceived by the viewer with a stereoscopic spatial impression, because a beam bundle 907 issuing from the object and extending on the left, in respect of a central plane 906 of the microscope, to a collective lens 909 of the microscope enters the collective lens 909 on the left and is imaged into the left ocular 903, whereas a beam bundle 908 issuing from the object on the right, in respect of the central plane 906, also enters the collective lens 909 on the right and is imaged into the right ocular 904. The objective system furthermore comprises an a focal zoom system 911 for changing the magnification. The oculars 903, 904 each comprise a tube lens 913 and a Schmidt-Pechan prism 915. The Schmidt-Pechan prisms are required to provide a vertically and horizontally rectified image of the object, the orientation of which has been inverted by the objective.

The conventional stereomicroscope may also be used in eye surgery to view an eye fundus 916 of an eye 917 of a patient. For this purpose, an ophthalmoscopic lens 919 is positioned in front of the patient's eye and produces an intermediate image of the eye fundus 916 in the object plane 905 of the microscope. The intermediate image of the eye fundus is then viewed by the surgeon through the stereomicroscope.

In the configuration of the stereomicroscope and the ophthalmoscopic lens shown in FIG. 11, due to the change in the image orientation and the stereoscopic sightline through the ophthalmoscopic lens, the eye fundus is perceived by the surgeon vertically and horizontally inverted and, in addition, pseudo-stereoscopic, i.e., as far as the depth perception is concerned, front and back appear inverted to the surgeon. In order to remove this problem, the correct image orientation must be re-established, on the one hand, and, on the other hand, the two stereo channels of the microscope must be interchanged, i.e., the beam bundle 907 issuing from the object plane 905 on the left must be supplied to the right eye 902 of the surgeon, and the beam bundle 908 issuing on the right must be supplied to the left eye 901 of the surgeon.

SUMMARY OF INVENTION

A stereomicroscopy system is disclosed for viewing an object and/or an intermediate image produced of an object, in microsurgery. The stereomicroscopy system includes an objective system with an object plane for positioning the object and/or the intermediate image to be viewed. The stereomicroscopy system also includes a beam interchanging and image inverting system. The beam interchanging and image inverting system supplies a first beam bundle directed to the left from the object plane in the direction of the objective system to the right of the objective system. The beam interchanging and image inverting system also supplies a second beam bundle directed to the right from the object plane in the direction of the objective system to the left of the objective system. The beam interchanging and image inverting system also inverts image orientations of the two beam bundles. The beam interchanging and image inverting system includes at least one Porro prism of the second kind.

Other aspects and advantages of the invention will be apparent from the following description and the appended claims.

DETAILED DESCRIPTION

Figure 1:
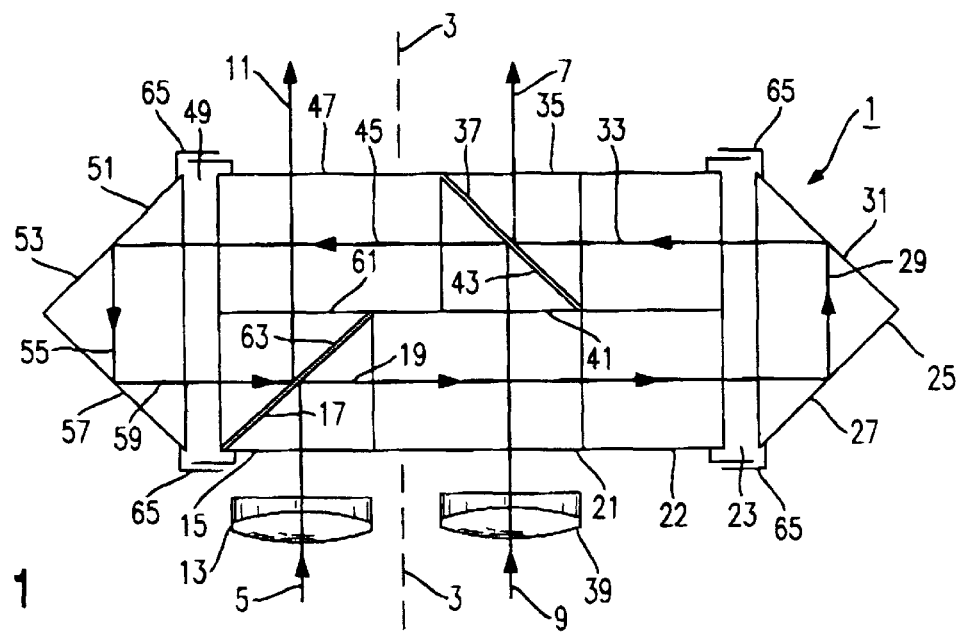
FIG. 1 shows a beam interchanging system for use in a stereomicroscopy system according to a first embodiment of the invention.

According to a first embodiment, the invention proceeds from a stereomicroscopy system comprising an objective system and an object plane for positioning therein the object or intermediate image to be viewed, a left ocular system to which a beam bundle is supplied which enters the objective system on the left, and a right ocular system to which a beam is supplied which enters the objective system on the right.

The invention may be distinguished in that a beam interchanging system is provided in beam paths of the ocular systems to interchange the stereo channels, i.e., to transfer the beam bundle supplied to the left ocular system to the right ocular system and to transfer the beam bundle supplied to the right ocular system to the left ocular system. However, the beam interchanging system does not change the image orientation, i.e., the beam bundle entering the beam interchanging system and the beam bundle emerging from the same have the same image orientation. No further system is provided either in the ocular system to change the image orientation.

One embodiment of the invention is based on the concept that, in the conventional stereomicroscope, an image inverting device is provided in the oculars or the tube, as has been explained in detail above. However, if, when viewing the intermediate image, this image inversion has already been effected by the ophthalmoscopic lens, no change of the image orientation must be effected in the tube. In order for the pseudo-stereoscopic effect of depth to be removed it is then merely required to interchange the two stereo channels, instead of effecting an image inversion.

In one embodiment, the beam interchanging system is removable from the beam paths of the ocular systems and replaceable by an image inverting system for inverting the image orientations of the beam bundles respectively supplied to the ocular systems without interchanging the stereo channels. Accordingly, the stereo microscopy system is transferable from a first viewing mode for viewing a vertically and horizontally inverted intermediate image, wherein the beam interchanging system is inserted in the beam paths of the ocular systems, to a second viewing mode for viewing an object in the object plane, wherein the image inverting system is inserted in the beam paths.

In this respect, it may be advantageous for optically effective media and geometries of the beam interchanging system and the image inversion system to be adjusted to one another such that beam bundles traversing said systems are focused substantially to the same ocular intermediate image positions. By this, it is accomplished that substantially no refocusing of the stereo microscopy system may be necessary when changing from one viewing mode to the other in order to obtain a sharp image for both eyes of the viewer.

More particularly, it may also be possible to accommodate the beam interchanging system or/and the image inverting system in a convergent or a divergent beam path of the ocular systems in place-saving fashion, which ocular systems may in particular be provided as binocular Keplerian telescopes.

Furthermore, it is advantageous to enable an adjustment of the ocular intermediate image positions in that an adjustment device is provided at the beam interchanging system for setting a difference which the beam interchanging system provides for the beam bundles supplied to the same in respect of the optical path lengths traveled by the same in the beam interchanging system to a desired value. In particular, said desired value may be substantially zero, i.e., both beam bundles travel substantially the same optical path length through the beam interchanging system, but may inevitably deviate slightly from one another as a result of unavoidable manufacturing tolerances of the optical components.

It is advantageous for the beam interchanging system to comprise (for both beam bundles supplied to the same, namely the left beam bundle and the right beam bundle) optically effective components which act symmetrically on the same in respect of a central plane between said two beam bundles as well as components which act asymmetrically on the beam bundles. In one embodiment, there is a beam interchanging system, the left beam bundle is first deflected to the right by a mirror, while the right beam bundle is first deflected to the left by a further mirror. These two mirrors thus act symmetrically on the two beam bundles in respect of the central plane. Subsequently, the left beam bundle is deflected twice to the left by means of two successive mirrors, while the right beam bundle is likewise deflected twice to the left by two successive mirrors. These two mirror pairs thus act asymmetrically on the two beam bundles in respect of the central plane. The left beam bundle is then again deflected to the right by a still further mirror, while the right beam bundle is again deflected to the left by a still further mirror, before the two beam bundles leave the beam interchanging system. The two last-mentioned mirrors again act symmetrically on the two beam bundles.

According to a second embodiment, the invention proceeds from a stereomicroscopy system comprising an objective system and an object plane for positioning therein an object or intermediate image to be viewed, a beam interchanging and beam inverting system being disposed between the object plane and entry lens of the objective system. The beam interchanging and beam inverting system supplies a beam bundle oriented to the left in the direction of the objective system in respect of a central plane to the right of the objective system, and it supplies a beam bundle oriented to the right in the direction of the objective system in respect of the central plane to the left of the objective system. Furthermore, it inverts the image orientations of each beam bundle. As a result, the stereomicroscopy system is particularly suitable for viewing a vertically and horizontally inverted intermediate images.

In this respect, the beam interchanging and image inverting system according to the invention comprises at least one Porro prism of the second kind.

It has been found that the Porro prism of the second kind is a particularly effective optical component for shifting the entering and emerging beam bundles, which shift is required for the beam interchange, and, at the same time, for achieving the desired image inversion. The Porro prism of the second kind is relatively compact and has a relatively short optical path length, so that an obstruction of the free working field and also visible distortions of the image viewed, such as image field restrictions, are minimized.

Preferably, one Porro prism of the second kind is provided for each one of the two beam bundles which is separately associated to each one of the same. As a result, the image inversion and beam interchange is accomplished with optical components which contribute to the entire light path of the beam bundles with only a relatively short optical path length.

A configuration which provides an alternative to this is advantageous if the stereomicroscopy system is designed to be utilized by two viewers. Beam bundles supplied to the objective system on the left and right in respect of a central plane are then imaged to the left and right eye, respectively, of a first viewer, while beam bundles supplied to the objective system centrally in respect of the central plane on the top and the bottom are imaged to the left and the right eye, respectively, of the second viewer.

Preferably, in such a configuration, a first Porro prism of the second kind is provided to image the beam bundles supplied on the left and right for the first viewer and the beam bundle supplied at the bottom for the second viewer, whereas a second Porro prism of the second kind is provided to image the beam bundle supplied at the top for the second viewer. As a result, a simple configuration is provided which accomplishes the beam interchange and image inversion for two independent viewers in simple manner.

According to a third embodiment, the invention proceeds from a stereomicroscopy system for alternately viewing a first object positioned in an object plane, for example, the cornea of an eye, and an intermediate image of a second object imaged into the object plane, for example, an eye fundus. In order to view the intermediate image of the second object, an inverting lens system, for example, an ophthalmoscopic attachment is inserted in the beam path in front of the object for producing the vertically and horizontally inverted intermediate image of the second object, as well as a beam interchanging and image inverting system for image inversion and pupil interchange of the intermediate image. In order to view the first object, the two components, namely the beam interchanging and image inverting system and the inverting lens system, are removed from the beam path between eye and objective.

According to an embodiment of the invention, the distance between the objective and the objects does not need to be substantially altered when changing from one viewing mode to the other one in order to obtain sharp images of the first object, for example, the area of the cornea, on the one hand, and of the second object, for example, the area of the eye fundus, on the other hand. According to an embodiment the invention, this is accomplished in that the geometric dimensions and optical media of the beam interchanging and image inverting system and the focal lengths of the inverting lens system are accordingly adjusted to one another.

What may be essential in this respect is that, above all, the optical path length of the beam interchanging and image inverting system is configured, for example, by carefully selecting the optical components used for this purpose, such that the object plane is spaced apart from the objective, when the beam interchanging and image inverting system is inserted in the beam path, by a distance which differs from the distance of the object plane from the objective, when the beam interchanging and image inverting system is removed from the beam path, said distance being determined by the desired viewing positions and here, in particular, by distances between the objects to be viewed and/or auxiliary means used to view the same. In eye surgery, the distance relevant here between the objects to be viewed may be the distance between the cornea and the intermediate image of the eye fundus, and the auxiliary means used to view the object may be the ophthalmoscopic attachment.

The distance between objective and object plane, with the beam interchanging and image inverting system being inserted in the beam path, may be different from the distance between objective and object plane with the beam interchanging and image inverting system being removed from the beam path. In one embodiment, the difference between these two distances is in the range of from about 15 mm to about 40 mm, in another embodiment from about 20 mm to about 30 mm, and in another embodiment from about 24 mm to about 26 mm.

According to a fourth embodiment, the invention proceeds from a stereomicroscopy system comprising an objective system and an object plane for positioning the object to be viewed or the intermediate image and a left and right ocular system as well as a beam interchanging and image inverting system which supplies a beam bundle entering the objective system on the left in respect of a central plane to the right ocular system, and, correspondingly, a beam bundle entering the objective system on the right to the left ocular system and, at the same time, inverts the image orientations of the two beam bundles respectively.

According to an embodiment of the invention, the beam interchanging and image inverting system comprises a pair of shortened Porro prisms of the second kind. As already explained above, the Porro prism of the second kind is particularly suitable to provide the beam shift required for the beam interchange and at the same time an image inversion. According to the invention, further improvements in image quality are achieved in that a so-called 'shortened' Porro prism of the second kind is used instead of the conventional Porro prism of the second kind. Performing the same optical task, namely beam shift and image inversion, this shortened Porro prism of the second kind provides a shorter optical path length as compared to the usual Porro prism of the second kind, so that various obstructions caused by the overall height and visible image distortions are minimized in the embodiment of the stereomicroscopy system of the invention.

According to a fifth embodiment, the invention proceeds from a stereomicroscopy system comprising an objective system and an object plane for positioning therein the object or intermediate image to be viewed, a left and right ocular system and a magnification changing system positioned in the beam path between the objective system and the ocular system as well as a beam interchanging and image inverting system.

According to an embodiment of the invention, the beam interchanging and image inverting system are provided in the beam path in front of the magnification changing system and behind the objective system. As a result, image interferences caused by the beam interchanging and image inverting system, such as vignetting, may be favourably minimized.

With reference to FIGS. 1 and 2, a stereomicroscope is described hereinafter as a first embodiment of the invention, said stereomicroscope being selectively employable in two viewing modes. In a first viewing mode, the stereomicroscope serves to view a vertically and horizontally inverted intermediate image, as it is, for example, produced by an ophthalmoscopic attachment for imaging an eye fundus in an object plane of the microscope. In a second viewing mode, the microscope serves to directly view an object positioned in the object plane.

The ophthalmoscopic attachment produces for a viewer a vertically and horizontally inverted image of the eye fundus as intermediate image in pseudo-stereoscopic spatial representation. In order to avoid this disturbing effect, a beam interchanging system 1 according to FIG. 1 is inserted into the beam path of the stereomicroscope. The beam interchanging system transforms a beam bundle 5 entering the beam interchanging system on the left in respect of a central plane 3 into a beam bundle 7 emerging from the beam interchanging system on the right, and it transforms a beam bundle 9 entering the beam interchanging system 1 on the right in respect of the central plane 3 into a beam bundle 11 emerging on the left of the beam interchanging system in respect of the central plane 3. Here, the entering beam bundles 5, 9 and the emerging beam bundles 7, 11 exhibit the same image orientation, i.e., an image inversion is not effected by the beam interchanging system 1.

The beam interchanging system 1 is comprised of glass blocks and glass prisms, the inner surfaces of which reflect the beam bundles.

The beam path in the beam interchanging system 1 is shown in FIG. 1 on the basis of the path of central beams of the beam bundles 5 and 9.

Having traversed a tube lens 13 of a left ocular system of the stereomicroscope, the beam 5 enters a 90° prism 15. The 90° prism 15 comprises a mirror surface 17 disposed at 45° in respect of the direction of the beam 5 such that the beam 5 is reflected by 90° to the right to form a beam 19. The beam 19 emerges from the 90° prism 15 and traverses successively two glass blocks 21 and 22, the 90° prism 15 and the glass blocks 21, 22 being cemented to each other. Having emerged from the glass block 22, the beam 19 passes through an air gap 23 and then enters a 180° prism 25. The beam 19 is reflected at a first mirror surface 27 of the 180° prism 25 by 90° to the left to form a beam 29 which thus propagates parallel to the original direction of the beam 5 and then impinges on a second mirror surface 31 of the 180° prism 25 which reflects the same by another 90° to the left to form a beam 33 which extends anti-parallel to the direction of the beam 19. The beam 33 emerges from the 180° prism 25 and first traverses the air gap 23, then the glass block 22 and subsequently enters a 90° prism 35 which is cemented to the glass block 22. At a mirror surface 37 of the 90° prism 35 the beam 33 is reflected by 90° to the right and emerges from the 90° prism 35 and thus from the beam interchanging system 1 as beam 7 into the right ocular system.

After having traversed a tube lens 39 of the right ocular system from the bottom to the top, the central beam of the right beam bundle enters the glass block 21, traverses the same and then enters a 90° prism 41 comprising a mirror surface 43 at which the beam 9 is reflected by 90° to the left to form a beam 45. The 90° prism 41 is cemented to the glass block 21. Furthermore, the 90° prisms 41 and 35 are joined such that their mirror surfaces 43 and 37 are spaced apart from another by only a small distance. Having emerged from the 90° prism 41, the beam 45 traverses a glass block 47 cemented to the 90° prism 41, then traverses an air gap 49 and enters a 180° prism. The beam 45 is reflected by 90° to the left at a mirror surface 53 of the 180° prism 51 to form a beam 55 which thus propagates anti-parallel to the direction of the beam 9 and is then reflected again by 90° to the left to form a beam 59 by a second mirror surface 57 of the 180° prism 53, so that it propagates anti-parallel to the beam 45. Having emerged from the 180° prism 53, the beam 59 traverses the air gap 49 and enters a 90° prism 61 having a mirror surface 63 at which it is again reflected by 90° to the left and, having again traversed the glass block 47 as beam 11, emerges from the beam interchanging system 1 into the left ocular system as beam 11.

The optical path lengths which the two beam bundles travel in the beam interchanging system between their entry as beam 5 and emergence as beam 7 and entry as beam 9 and emergence as beam 11, respectively, may be substantially equal, which may be accomplished by the above-described configuration of the glass prisms and glass blocks. The glass blocks 21 and 47 are traversed by both beam bundles, while the glass block 22 is merely traversed by the beam bundle which enters the beam interchanging system 1 as beam 5 and emerges from the same as beam 7. The latter glass block 22 serves to compensate for the optical path length which the other beam bundle must additionally travel, because it travels as beam 55 over a certain distance opposite to the original direction of the beam 9 from bottom to top, while the beam bundle which enters as beam 5 never propagates into a direction opposite to the original beam direction.

In order to achieve a fine adjustment of the optical path lengths which both beam bundles travel in the beam interchanging system 1, the air gaps 23 and 49 are provided which are adjustable by means of adjustment means 65 which couple the 180° prism 25 to the glass block 22 and the 180° prism 57 to the glass block 47 and the 90° prism 15, respectively.

Figures 2A, 2B:
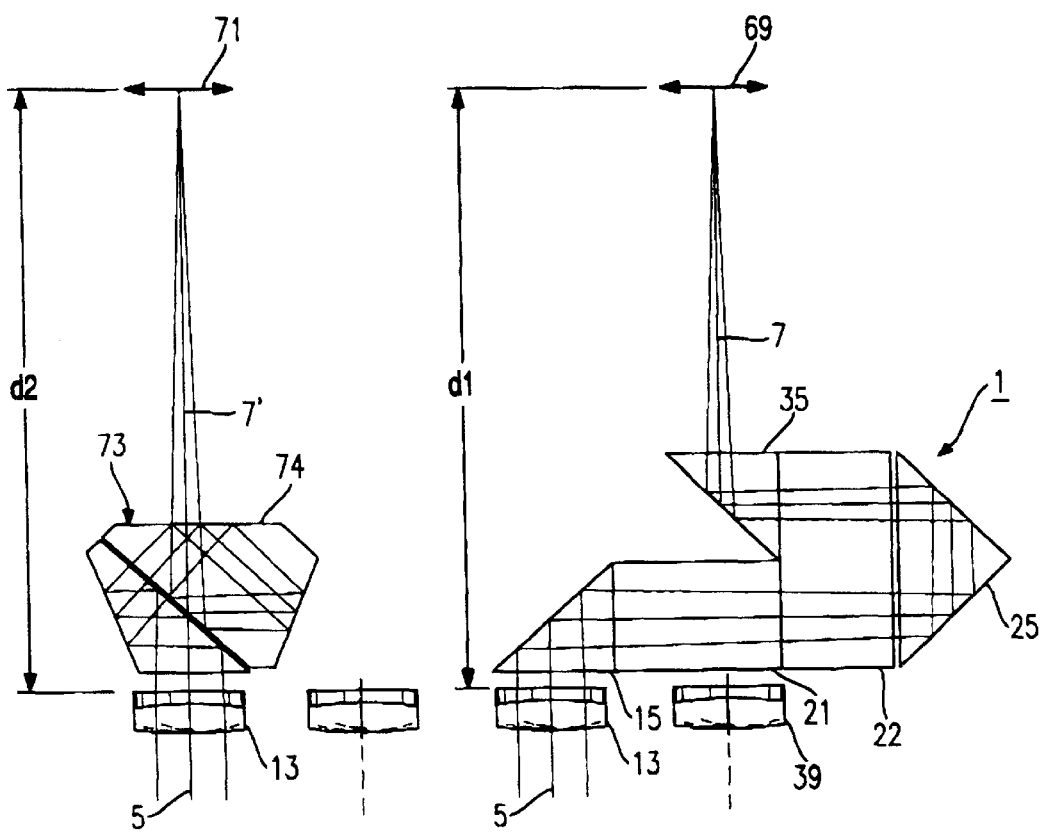
FIG. 2a is a partial view of the beam interchanging system of FIG. 1 positioned in a convergent beam path.
FIG. 2b shows the convergent beam path of FIG. 2a, with the beam interchanging system being removed from the beam path and an image inverting system being inserted instead.

As is evident from FIG. 2a, the left beam bundle 5 enters the tube lens 13 of the left ocular system as parallel beam bundle and is transformed by the same to a convergent beam bundle, so that in an intermediate image plane of the right stereo channel a sharp intermediate image is formed in the intermediate plane 69. The intermediate image plane 69 is disposed in the focus of the tube lens 13 at a distance d1 which is defined by the refractive index of the glass used for the prisms 15, 25, 35 and the glass blocks 21, 22, the geometric dimensions thereof as well as the dimensions of the traversed air paths.

If the stereomicroscope is to be employed in the other viewing mode, wherein the ophthalmoscopic lens is removed from the beam path and the object to be viewed is positioned in the object plane of the microscope, a beam interchange by the beam interchanging system 1 is not required any more, so that it may be removed from the beam path. However, without inverting prism the object positioned in the object plane would then be perceived vertically and horizontally inverted by the viewer. In order to provide a vertically and horizontally correct image of the object positioned in the object plane, in this viewing mode, an image inverting system 73 is therefore provided in the beam path instead of the beam interchanging system 1, as seen in FIG. 2b. Said image inverting system 73 causes the beam bundle 5 extending through the left ocular system to remain in the left ocular system and to be focused in an intermediate image plane 71 of the left ocular system as beam bundle 7', the beam bundle 9 extending through the right ocular system also remaining in the same and being focused there in a corresponding intermediate plane. To this end, the image inverting system 73 comprises one Schmidt-Pechan prism with roof edge 74 for each one of the left ocular system and the right ocular system.

The geometric dimensions of the Schmidt-Pechan prism 74 as well as the refractive index of the glass used for the same determine a distance d2 between the tube lens 13 of the left ocular system and the intermediate image plane 71 in the second viewing mode. By appropriately adjusting the adjustment devices 65 of the beam interchanging system 1, it is possible to render the distances d1 and d2 equal, so that, when the viewing mode is changed, a re-adjustment of the ocular system is not required in order to obtain a sharp image.

The same applies to the distances at which an intermediate image plane of the right beam bundle 9 is spaced apart from the tube lens 39, the appertaining beam paths not being shown in FIGS. 2a and 2b for reasons of clarity.

In the following, variants of the stereomicroscope shown in FIGS. 1 and 2 will be described. Components which correspond to each other in structure and function are designated by the same reference numerals as used in FIGS. 1 and 2. However, in order to distinguish the same, an additional letter supplements them. For the purpose of illustration, reference is made to the entire above description.

Figure 3:
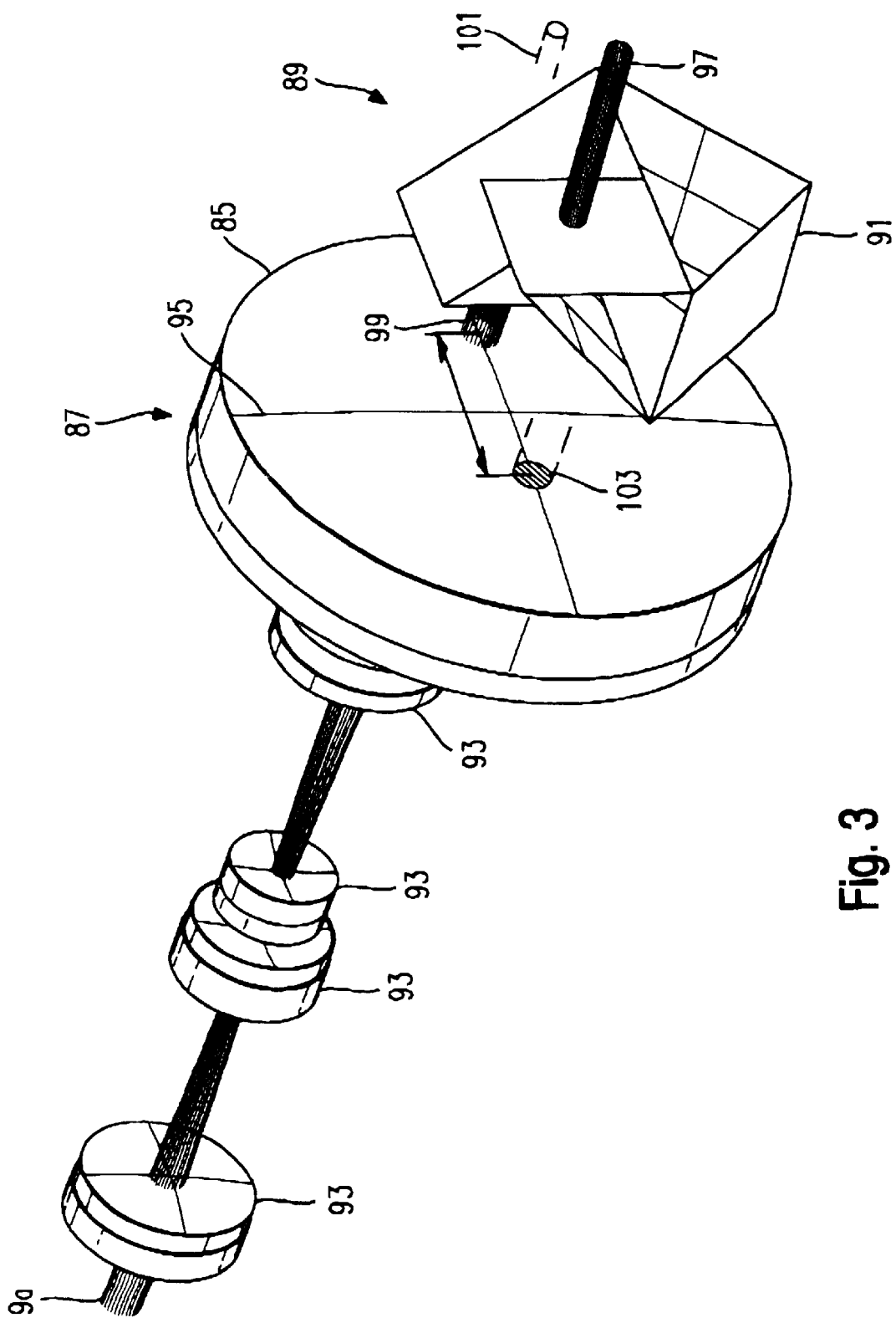
FIG. 3 is a partial view of a beam path of a stereomicroscopy system according to a second embodiment of the invention.

FIG. 3 shows a perspective partial view of a further embodiment of the invention, namely a stereomicroscope in the above-described first viewing mode, i.e., for viewing a vertically and horizontally inverted intermediate image in the object plane of the microscope.

To this end, a beam interchanging and image inverting system 89 comprised of two Porro prisms of the second kind is positioned in front of an entry lens 85 of an objective system 87 of the microscope. For reasons of clarity, only one Porro prism 91 of said two Porro prisms is shown in FIG. 3. In order to change the magnification, the objective system 87 further comprises a zoom system with several lenses 93. The Porro prism 91 of the second kind imparts a parallel shift to a beam bundle 97 extending on the left in respect of a central plane 95 of the objective system 87, said beam bundle issuing from the object plane and being directed to the entry lens 85, and supplies it to the right of the entry lens 85 in respect of the central plane 95 as beam bundle 99. Analogously, the second Porro prism of the second kind, not shown in FIG. 3, of the beam interchanging and image inverting system 89 imparts a parallel shift to a beam bundle 101 issuing from the object plane and being directed to the right of the entry lens 85 in respect of the central plane 95 to the left across the central plane 95 and supplies it to the left of the objective system 87 as beam bundle 103. The paths of the beam bundles 101 and 103 are merely outlined in FIG. 3 in dashed line.

The way in which the beam guidance is effected after the objective system results in the beam bundle 99 being imaged in the right ocular system of the microscope and, correspondingly, the beam bundle 103 in the left ocular system of the microscope.

The beam interchanging and image inverting system 89 comprises two identical Porro prisms of the second kind which are fitted into one another such that the backsides of the mirror surfaces of the small 90° prisms abut against one another back-to-back.

Figure 5:
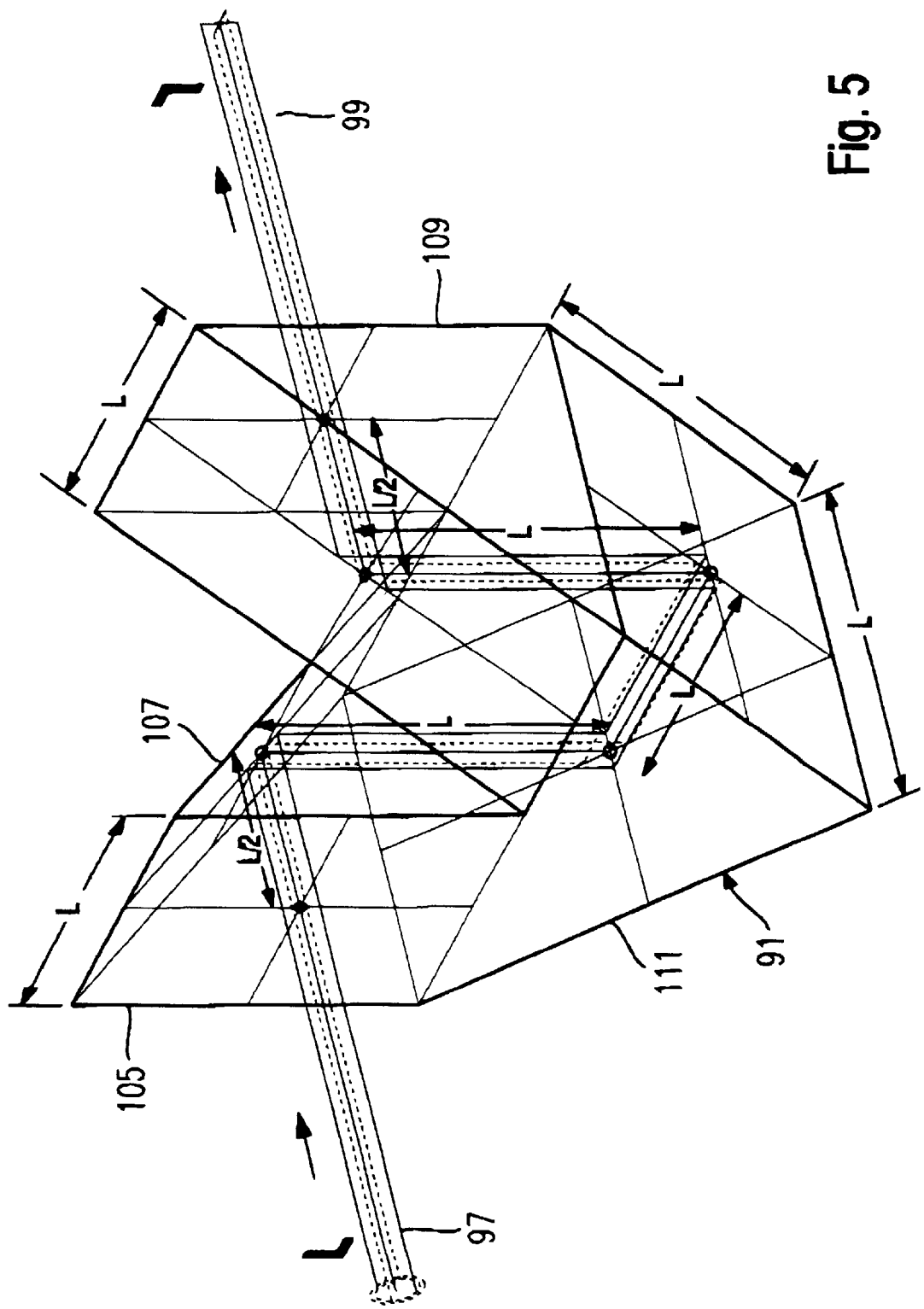
FIG. 5 shows a beam path through a Porro prism.

FIG. 5 shows an enlarged view of the beam path through the Porro prism of the second kind 91. Said Porro prism 91 may be conceived as being combined of two small 90° prisms 105 and 109 and a large 180° prism 111. The two 90° prisms 105 and 109 have a short edge with a length L. The beam 97 enters the first 90° prism 105 and travels a distance L/2 therein until it is reflected by 90° at a mirror surface 107 of the prism 105. The beam then travels a distance L/2 until it enters the 180° prism 111 in which it again travels a distance L/2 until its first reflection by 90° therein. Subsequently, the beam travels a distance L in the 180° prism 111 until it is further reflected by another 90° therein. The beam then travels a further distance L/2 until it emerges from the 180° prism 111 and enters the second 90° prism 109. In this prism, the beam again travels a distance L/2 until it is reflected by 90° at the mirror surface of the 90° prism 109 from which it emerges as beam 99 after having travelled a further distance L/2. It is apparent, that the beam thus travels a total geometric length of 4 L in the prism 91.

Figure 4:
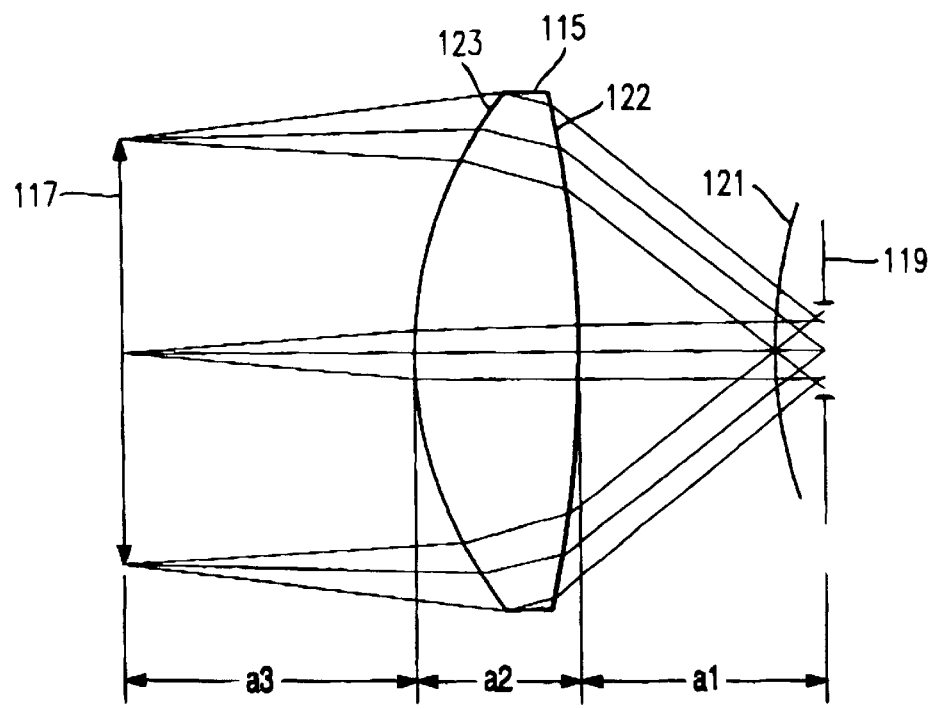
FIG. 4 is a schematic view of an ophthalmoscopic attachment for use in the stereomicroscopy system according to an embodiment of the invention.

FIG. 4 shows an ophthalmoscopic lens 115 for use in the stereomicroscope, said ophthalmoscopic lens being positioned in front of an eye of a patient in order to produce an image of an eye fundus in an object plane 117 of the stereomicroscope. Only a pupillary aperture 119 of the eye to be examined is schematically shown in FIG. 4 as well as a surface of a cornea 121. The lens 115 comprises a lens surface 122 facing towards the eye with a radius of curvature of about 42.474 mm and an aspherical lens surface 123 facing towards the object plane 117 with a radius of curvature of about 11.372 mm.

The center of the lens surface 122 facing towards the eye is spaced from the pupil 119 of the eye by a distance a1 of approximately 8.5 mm. The centers of the two lens surfaces 122 and 123 of the lens 115 are spaced apart from one another by a distance a2 of 5.6 mm, while the lens surface 123 is spaced apart from the object plane 117 by a distance a3 of 9.99 mm. Accordingly, the pupil 119 is spaced apart from the intermediate image plane by a distance of approximately 24.09 mm, the surface of the cornea 121 being typically spaced apart from the pupil plane by a distance of approximately 1 mm.

FIG. 6a shows the beam path and the position of the object plane 117 of the stereo microscope in the second viewing mode, i.e., in the mode in which the beam interchanging and image inverting system 89 is removed from the beam path, and the cornea of the eye to be operated is viewed with the microscope. Accordingly, the cornea 121 is also positioned in the object plane 117. The distance between the entry lens 85 and the object plane 117 is b1.

FIG. 6b shows the system in the first viewing mode in which the beam interchanging and image inverting system 89 is positioned in front of the entry lens 85 for viewing the vertically and horizontally inverted, pseudo-stereoscopic intermediate image of the eye fundus in the object plane 117 of the microscope, said intermediate image being produced by the ophthalmoscopic lens 115.

According to FIG. 4, said intermediate image is positioned in front of the eye pupil spaced apart by a distance B4=a1+a2+a3. The microscope must thus be focused onto this intermediate image plane in the first viewing mode. It thus constitutes the new object plane for the microscope in the first viewing mode.

Figure 6:
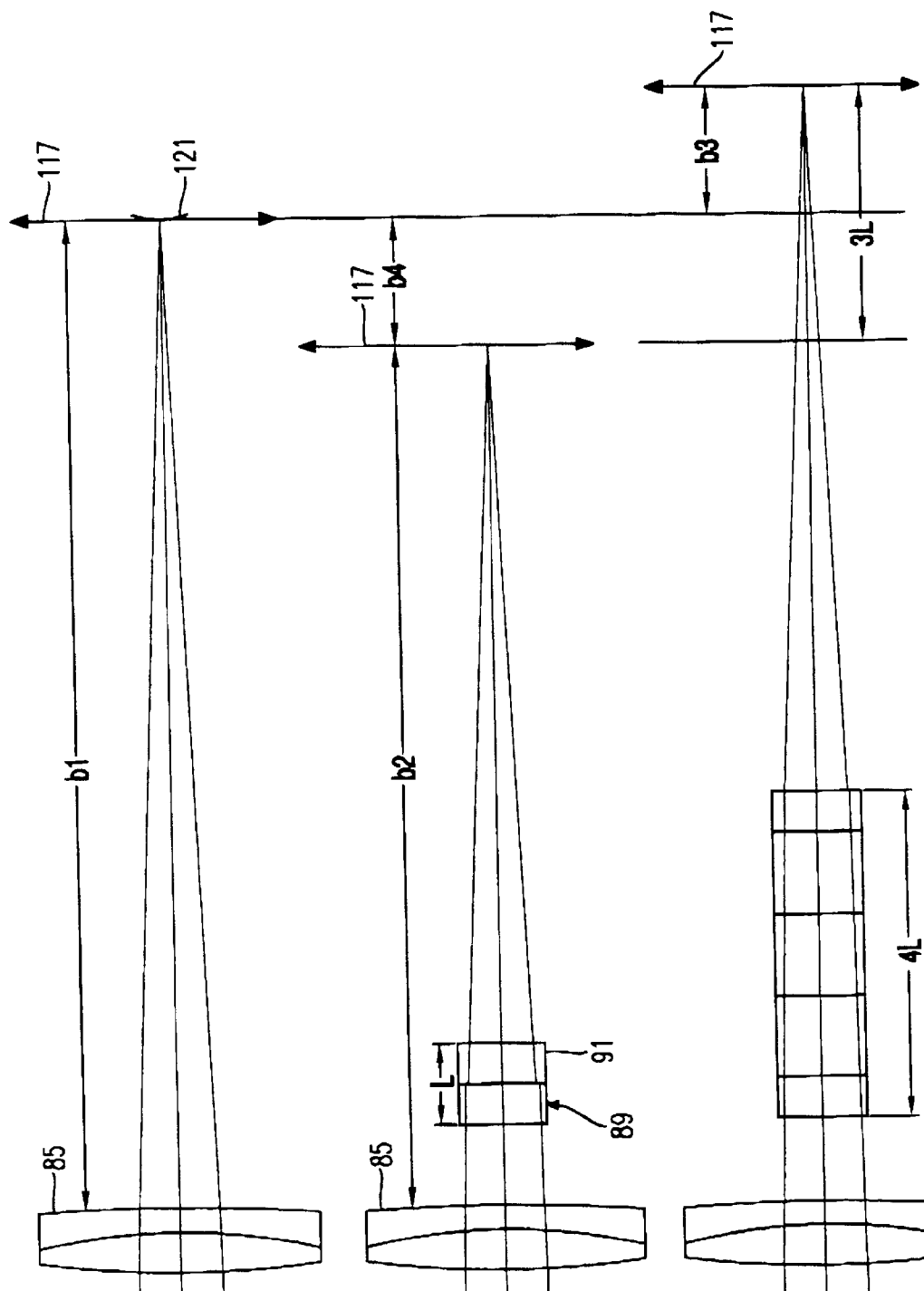
FIG. 6a shows the beam path between object plane and objective, with a beam interchanging and image inverting system being removed from the beam path of the embodiment shown in FIG. 3.
FIG. 6b is a representation corresponding to that of FIG. 6a, the beam interchanging and image inverting system being inserted in the beam path.
FIG. 6c is a representation corresponding to that of FIG. 6b, the beam path through the beam interchanging and image inverting system being depicted unfolded.

Due to the configuration of the Porro prism of the second kind 91 according to the invention, the object plane 117 viewed with the microscope can now be exactly shifted to a distance b2 from the entry lens 85 in the first viewing mode, so that the difference b1−b2=b4 (referring to FIG. 6). Accordingly, no refocusing is required when changing between the two viewing modes in order to obtain optimal image sharpness.

To illustrate this condition for the difference b1−b2, the beam path in the first viewing mode is shown in FIG. 6c such that the course of the beam through the Porro prism of the second kind 91 is shown unfolded.

For optical reasons, the object plane 117 is shifted by a glass block of the length 4L by b3=4L*(n−1)/n, on the one hand.

For mechanical reasons, due to the beam path being folded, the object plane is shifted by 3L in the opposite direction, on the other hand.

Both the refractive index n of the prism glass and the edge length L of the prism are thus decisive for the shift of the object plane by b4=3L−b3 to the intermediate image position of the eye fundus given by the ophthalmoscopic lens.

As an example, a shift by b4 of about 25.0 mm is indicated.

If the edge length L of the prism 91 is about 16.84 mm and use is made of a N-SK2 type glass of the company Schott having a refractive index of n of about 1.60994, the distance B3 is about 25.52 mm, so that with 3L equal to about 50.52 mm a shift of the object plane b4 of about 3L−b3 of about 25.0 mm is obtained.

By altering the glass and the edge length of the prism, this value can be varied as it is useful for practical purposes.

Hence, when changing from the second viewing mode, in which the microscope is focused onto the cornea of the eye, to the first viewing mode, in which the ophthalmoscopic lens 115 is positioned in front of the eye to view the image of the eye fundus, substantially no change of the distance between the objective lens 85 and the eye is required. This constitutes a great relief for the surgeon.

Figure 8:
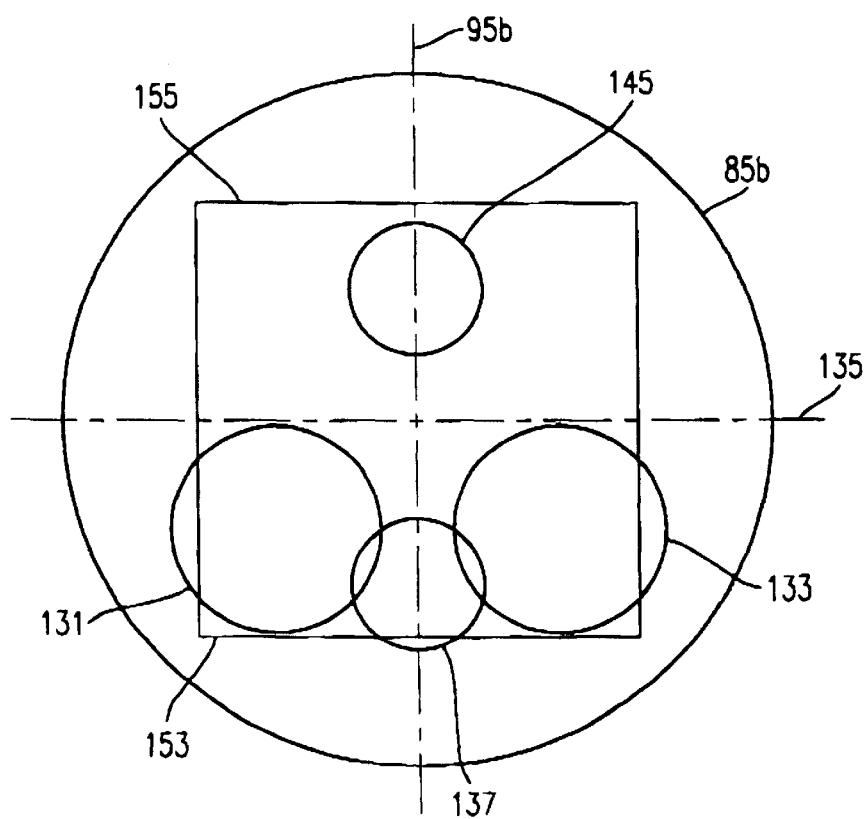
FIG. 8 schematically depicts the position of Porro prisms in front of the objective of the stereomicroscopy system shown in FIG. 7.
Figure 7:
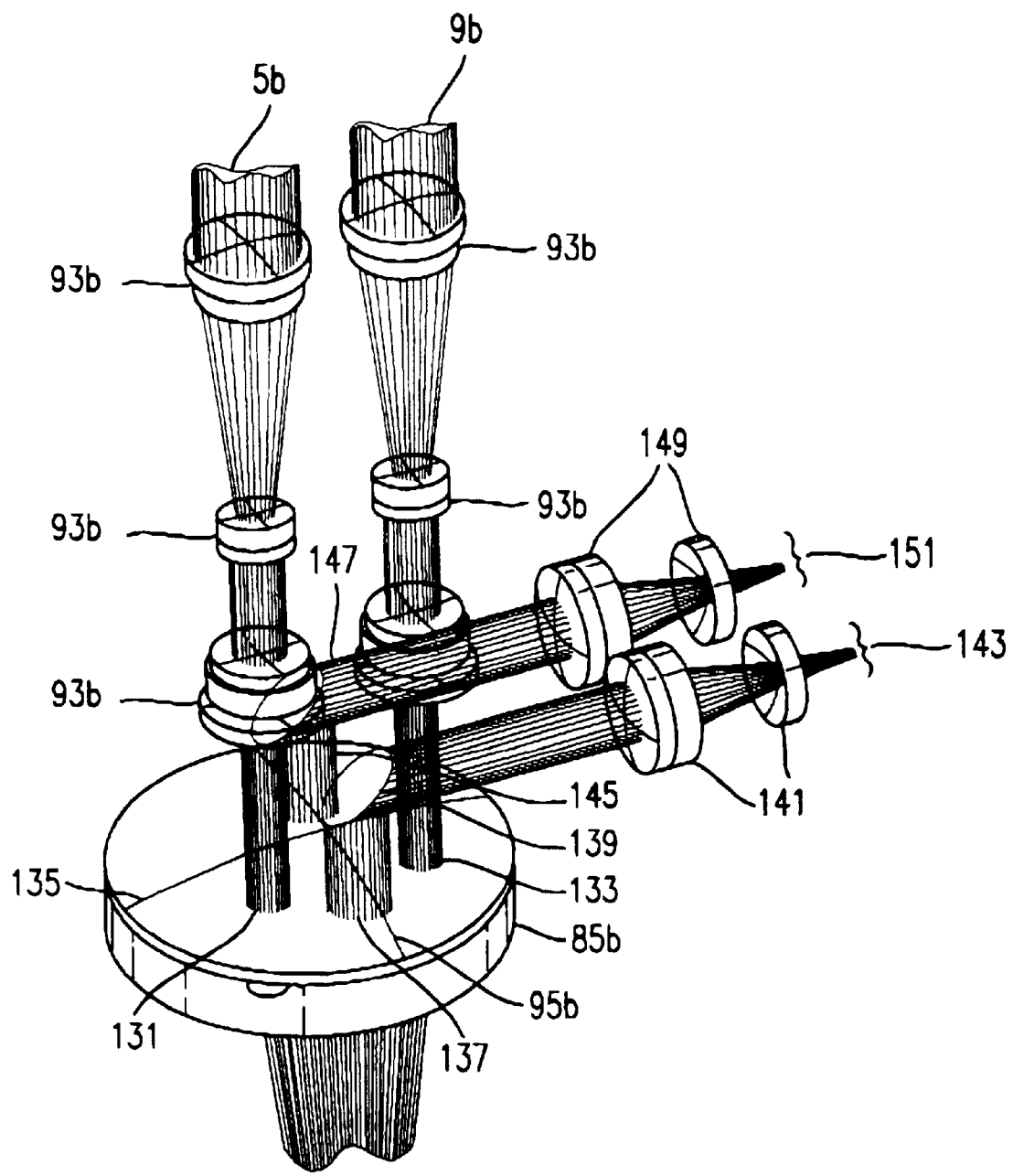
FIG. 7 is a detailed view of a beam path through a stereomicroscopy system according to a fourth embodiment of the invention.
Figure 9:
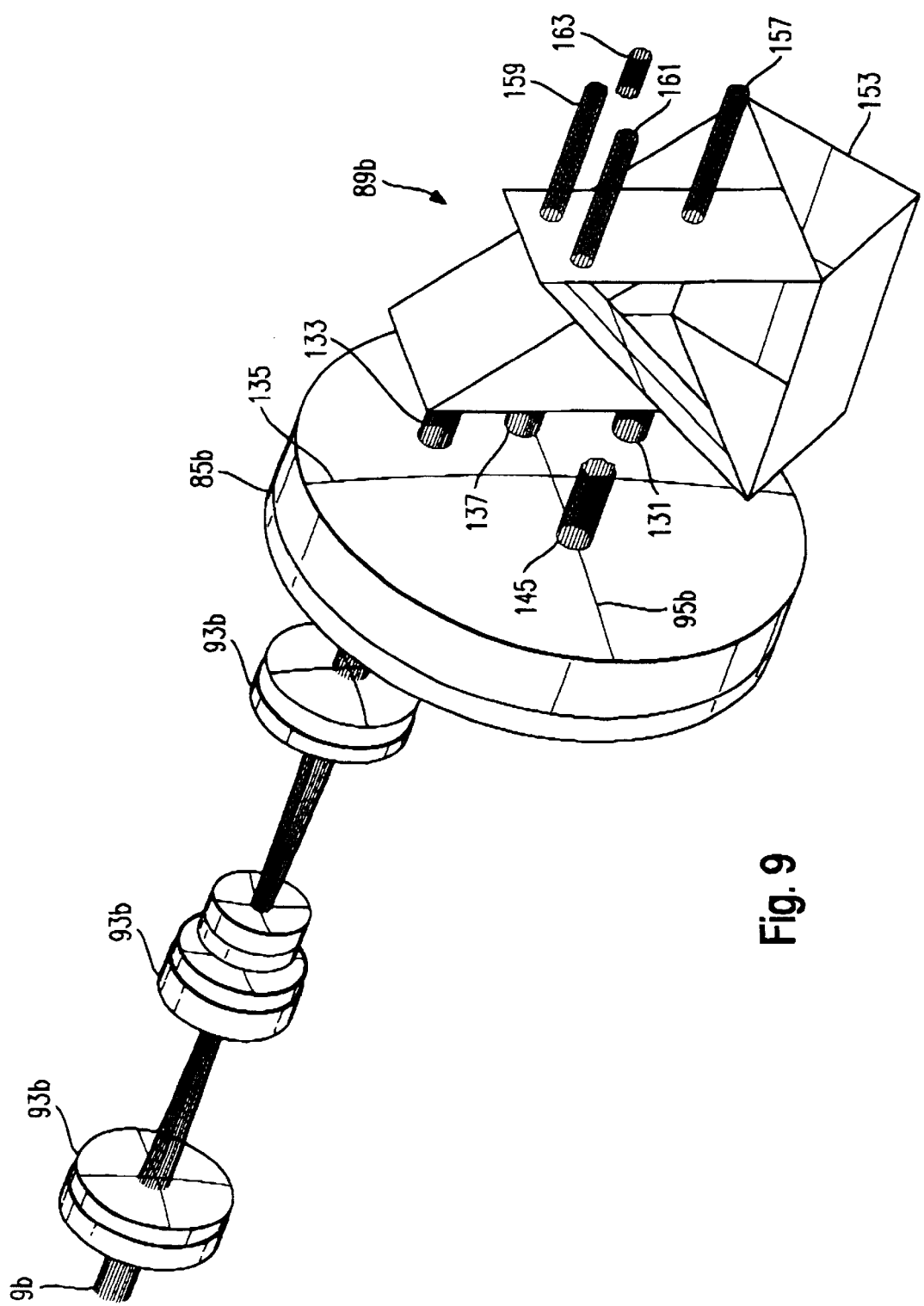
FIG. 9 is a partial spatial view of the embodiment shown in FIG. 7.

FIGS. 7 to 9 show a variant of the above-described embodiment which differs from the same primarily in that the stereomicroscope is not only provided for one viewer, i.e., provided with one pair of ocular systems, but that the microscope is much rather provided for two viewers, for which reason two pairs of stereoscopic viewing channels are provided with two oculars each.

FIG. 7 is a partial spatial view of the beam path of such a microscope illustrating how the corresponding beam bundles are supplied to the two pairs of ocular systems.

FIG. 7 shows a beam bundle 5b which is supplied to a left ocular of a first viewer as well as a beam bundle 9b which is supplied to the right ocular of the first viewer. The beam bundle 5b emerges as beam bundle 131 on the left of a central plane 95b of an objective lens 85b of the microscope, wherein it enters a zoom system of lenses 93b, and emerges therefrom as beam bundle 5b. Correspondingly, a beam bundle 133 emerges from the objective lens 85b on the right of the central plane 95b, said beam bundle likewise traversing zoom lenses 93b of the right stereo channel of the first co-user and enters the right ocular of the first viewer as beam bundle 9b.

A horizontal plane 135 extending perpendicular to the central plane 95b is depicted on the entry lens 85 in FIG. 7, the central plane 95b and the horizontal plane 135 thus dividing the entry lens 85b in equal quadrants.

A beam bundle 137 emerging beneath the horizontal plane 135 and centrally on the central plane 95b impinges on a mirror 139 positioned at 45° to the travel direction of the beam bundle 137, said mirror reflecting the beam bundle 137 by 90° to its original beam direction. The beam 137 then traverses a Galilean system of lenses 141 and is supplied to a left ocular of a second viewer as beam bundle 143. A beam bundle 145 emerging above the horizontal plane 135 and centrally on the central plane 95b from the entry lens 85b is also reflected by 90° at a further mirror 147 positioned parallel to the mirror 139 and traverses a further Galilean system of lenses 149 which is positioned in parallel to the Galilean system of the lenses 141 for the beam 137, the beam bundle 145 being then supplied to a right ocular of the second viewer as beam 151.

FIG. 8 shows projections of the cross-sections of the beam bundles 131, 133, 137 and 145, again in cross-section, in top plan view onto the lens surface of the lens 85b facing away from the object plane, the bundles 131 and 133 being shown for the large bundle cross-sections occurring in high magnification.

The beam bundles 131, 133, 137 and 145 as they enter the entry lens 85b of the object are evident from the perspective partial view of FIG. 9. Of the emerging beam bundles, merely the beam bundle with appertaining zoom lenses 93b is shown which propagates as beam bundle 9b into the right ocular of the first viewer. Before entering the entry lens 85b, the beam bundles 131, 133, 137 and 145 have passed through a beam interchanging and image inverting system 89b which provides both the necessary beam interchange and image inversion required for viewing a vertically and horizontally inverted intermediate image in the object plane.

The beam interchanging and image inverting system 89b of FIG. 9 comprises two Porro prisms of the second kind 153 and 155. In the perspective representation of FIG. 9, merely the prism 153 is shown, whereas projections of both prisms 153 and 155 are evident from FIG. 8.

The beam interchange and image inversion of the two beam bundles 5b and 9b supplied to the oculars of the first viewer is accomplished by the prism 153. To this end, a beam bundle 157 issuing from the object plane and directed to the entry lens 85b on the left of the central plane 95b is shifted by the prism 153 such that it emerges from the prism 153 as beam bundle 133 which enters the objective on the right of the central plane 95b and is destined as beam bundle 9b for the right eye of the first viewer. Correspondingly, a beam bundle 159 directed to the entry lens 85b on right of the central plane 95b enters the prism 153 and emerges from the same as beam bundles 131 which is destined for the left eye of the first viewer.

Furthermore, a beam bundle 161 enters the prism 153 which is centrally directed onto the central plane 95b and above the horizontal plane 135 to the entry lens 85b. The prism 153 shifts this beam bundle 161 such that it enters the objective centrally on the central plane 95b and below the horizontal plane 135 as beam bundle 137, as is evident from FIG. 8.

As already described above, the beam bundle 137 is destined for the left eye of the second viewer.

The second prism 155 of the beam interchanging and image inverting system 89b is merely traversed by a beam bundles 163, the spatial positioning of which in respect of the other beam bundles 157, 159 and 161 is evident from FIG. 9. The beam bundle 163 is directed centrally in respect of the central plane 95b and below the horizontal plane 135 onto the entry lens 85b of the objective. The prism 155 serves to shift the beam bundle 163 such that it enters the objective centrally in respect of the central plane 95b and above the horizontal plane 135 as beam bundle 145, as it is likewise outlined in FIG. 9.

FIG. 8 shows the projected emergent surfaces of both prisms 153 and 155. It thus follows from FIG. 8 that the two beam bundles 131 and 133 destined for the left and the right eyes of the first viewer as well as the beam bundle 137 destined for the right eye of the second viewer emerge from the Porro prism of the second kind 153. Merely the beam bundle 145 destined for the left eye of the second viewer emerges from the prism 155.

With this configuration, a beam interchanging and image inverting system insertable in front of the objective of the microscope is realized which requires comparatively little space and thus provides minimum obstruction as regards the access to the operating field. Moreover, the beam interchange and image inversion for the first viewer is effected by an integral prism, so that the viewer is not confronted with the problem of adjusting the image positions for the left and right eye relative to one another. However, two identical Porro prisms of the second kind can also be fitted into one another with such a precision and can be adjusted relative to one another that for the second user, too, whose two stereo channels employ both prisms, image position problems are largely avoidable.

Figure 10:
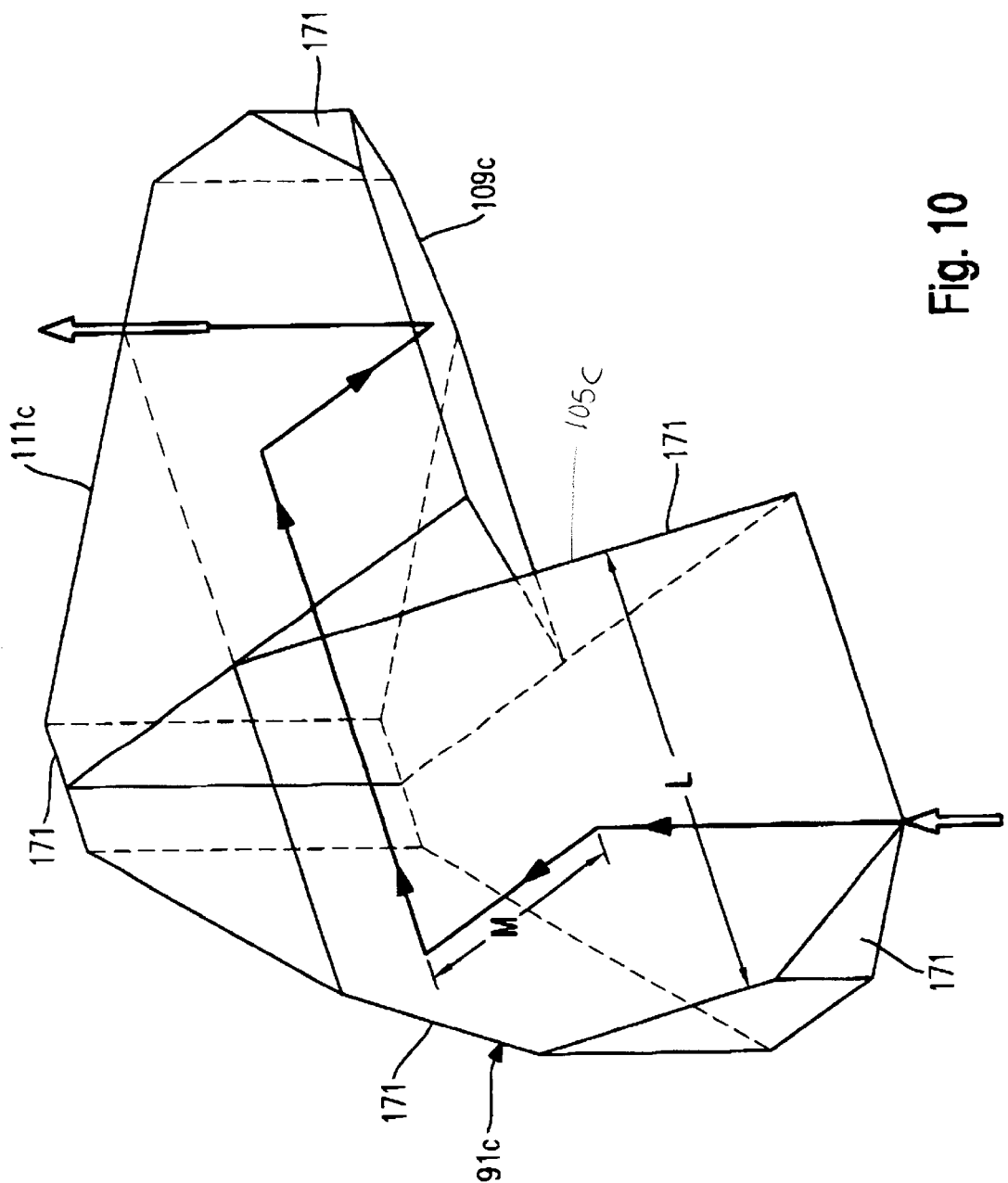
FIG. 10 shows a shortened Porro prism for use in a further embodiment of the stereomicroscopy system of the invention.

FIG. 10 shows a 'shortened' Porro prism of the second kind 91c which is known. This prism, too, can be conceived as being composed of two 90° prisms 105c and 109c and a 180° prism 111c. In contrast to the Porro prism of the second kind shown in FIG. 5, in the prism 91c of FIG. 10, the vertex of the 180° prism 111c is shortened so that its reflecting surfaces are closer to the 90° prisms 105c and 109c. Moreover, all partial prisms 105c, 109c, 111c of the prisms 91c have broken edges 171 which are not traversed by the beam bundle to be reflected. As is evident from FIG. 10, a central beam travels a distance M between its reflection at the 90° prism 105c and its first reflection at the 180° prism 111c, which distance is calculated M=0.71 L, with L being again an edge length of the 90° prism 105c, 109c.

Accordingly, the distance which a beam travels in the prism 91c is 3.42 L which, as compared to the value of 4L for the prism of FIG. 5, is a shortened optical path length. At the same time, the prism 91c likewise acts as beam interchanging and image inverting system which is insertable in a stereomicroscope for viewing a vertically and horizontally inverted intermediate image.

The shortened Porro prism of the second kind may be used at different locations of the microscope. It may be positioned in front of the objective, as it has already been described for the usual Porro prism of the second kind with reference to the embodiments shown in FIGS. 3 and 9.

Figure 11:
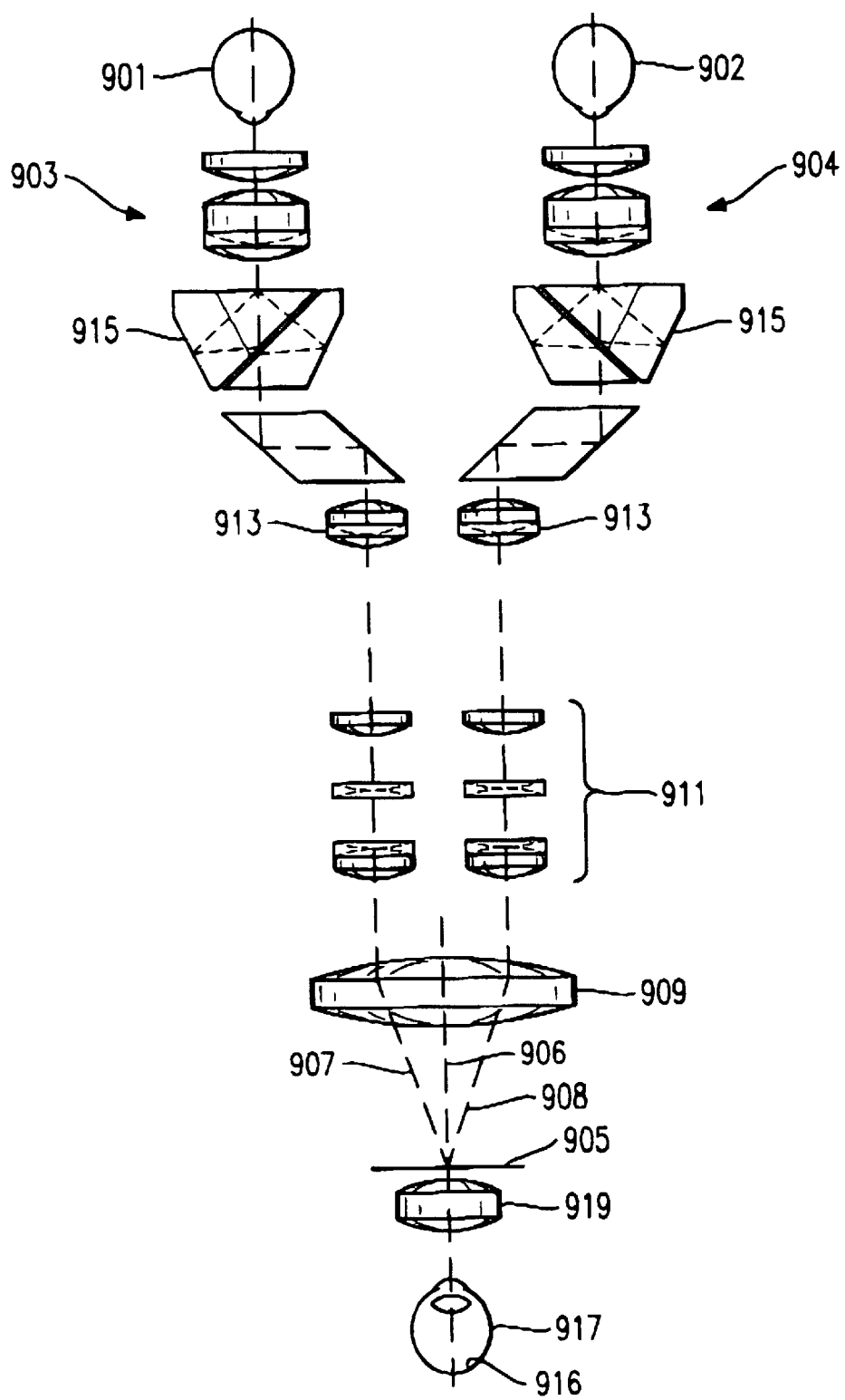
FIG. 11 shows a stereomicroscopy system according to the prior art.

Moreover, the shortened Porro prism of the second kind may be employed in the beam path between the objective and the oculars for beam interchange and image inversion, i.e., in a comparison with FIG. 11 already referred to at the outset, between the elements 909 and 913. In this respect, an arrangement between a magnification changing system and the oculars is also possible (between components 911 and 913 of FIG. 11). However, in another embodiment, there is provided an arrangement between the objective or the collective lens of the objective and the magnification changing system (between the components 909 and 911 of FIG. 11). Such a configuration is particularly preferred because at this location there is minimum interference of the produced image, such as vignetting.

Figure 12:
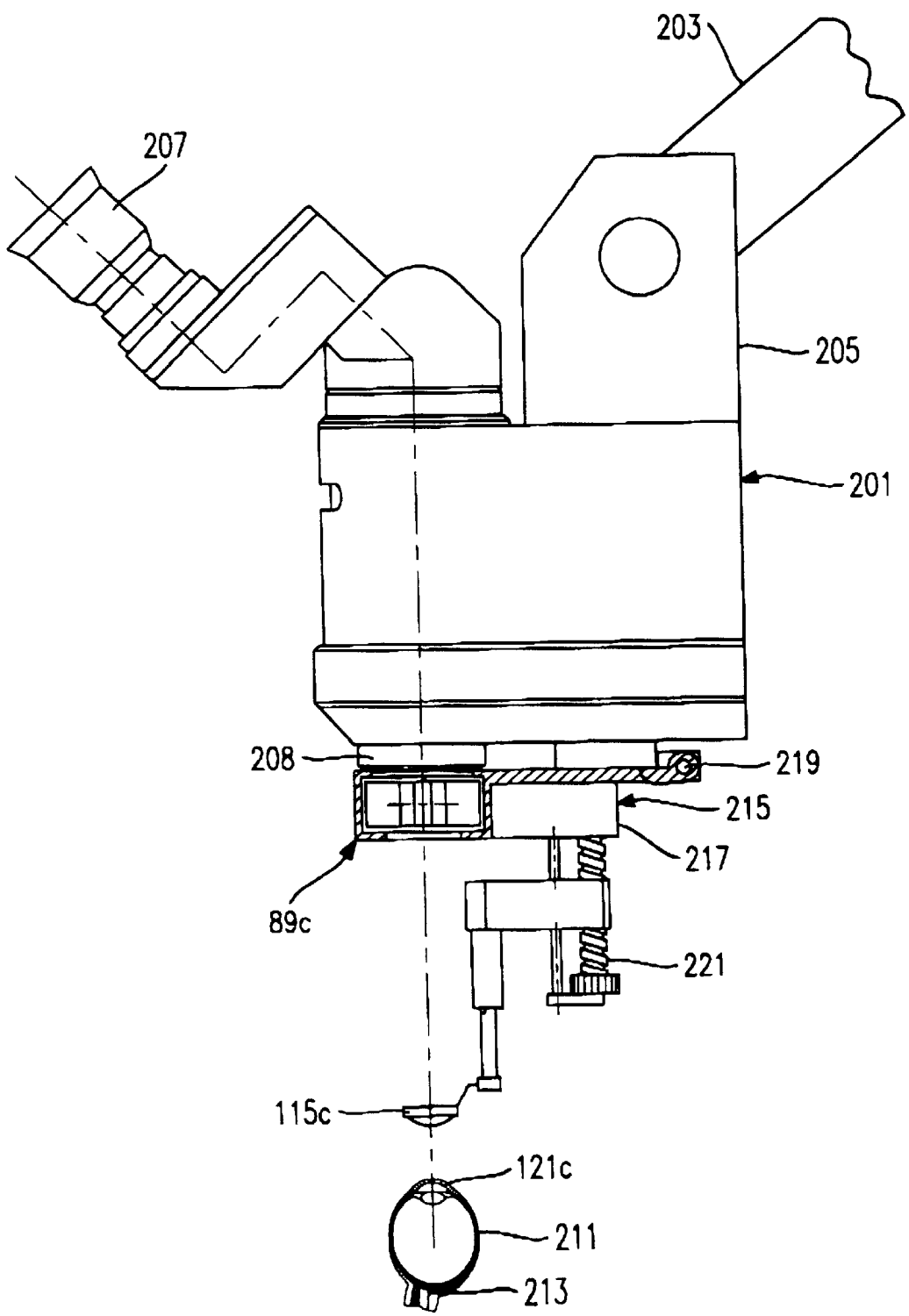
FIG. 12 a side view of a stereomicroscopy system according to a further embodiment of the invention.

FIG. 12 is a side view of a stereomicroscope 201 comprising a beam interchanging and image inverting system 89c. A microscope body 205 is pivotably mounted on a stand 203 and supports a pair of oculars 207 and an objective 208, the lens systems included in the oculars 207 and the objective 208 as well as further lens systems included in the microscope body 205 are not shown in FIG. 12. The structure of said lens systems may be of the kind as described in respect of FIGS. 3 to 11, but other lens configurations are also possible. The stereomicroscope 201 serves to view an eye 211 of a patient. In particular, an eye fundus 213 may be observed through a cornea 121c of the eye. To this end, the microscope 201 comprises an attachment system 215 mounted at the microscope body 205. As optical components, the attachment system 215 comprises the beam interchanging and image inverting system 89c positioned in front of the objective 208 as well as an ophthalmoscopic lens 115c positioned between the beam interchanging and image inverting system 89c and the cornea 121c. The beam interchanging and image inverting system 89c and the ophthalmoscopic lens 115c are attached to a common support 217 which, in turn, are mounted to the microscope body 205. The support 217 is mounted at the microscope body 205 to be pivotable about an axis 219 such that the optical system comprised of beam interchanging and image inverting system 89c and ophthalmoscopic lens 115c is pivotably insertable into and removable from the beam path of the microscope with ease. In order to provide a simple adjustment of the image of the eye fundus 213 produced by the microscope 210, the distance between the ophthalmoscopic lens 115 and the beam interchanging and image inverting system 89c is variable by means of a spindle drive 221.

In the above-described embodiment of FIG. 12, the beam interchanging and image inverting system and the ophthalmoscopic lens 115 are commonly mounted to be pivotably insertable into the beam path of the microscope. However, it is also possible to mount the ophthalmoscopic lens separately from the microscope, for example, at a stand, and to pivotably mount the beam interchanging and image inverting system at the microscope. Equally, it is possible to deviate from the pivot mount shown in FIG. 12, and to provide, for example, one or more pivot axes with different orientation. Moreover, it is possible, to mount the attachment system on a carriage, for example, in order to insert it into the beam path and to remove it therefrom.

The image interchanging system of the embodiment shown in FIG. 1 is positioned in the embodiment described with reference to FIG. 1 in the beam path of the ocular systems of the stereomicroscope. However, this beam interchanging system can also be employed at any other location of the beam path of the stereomicroscope to obtain the desired effect, namely a beam interchange, with the image orientation being maintained.

Moreover, the use of this beam interchanging system, i.e., the configuration described with reference to FIG. 1, of two 90° mirrors and a 180° double mirror per beam path is not restricted to the use in stereomicroscopes. Rather, the use of this beam interchanging system is contemplated for any other optical field in which the problem of a beam interchange, with the image orientation being maintained, is encountered.

The above embodiments have been described as using an ophthalmoscopic lens for producing a vertically and horizontally inverted intermediate image of the fundus of an eye in order to produce the intermediate image in the objective plane of the microscope. However, the described microscope can also be used for any other application in which the problem of viewing a vertically and horizontally inverted intermediate image in the object plane of the microscope is encountered. For example, this could be other surgical applications or any other application for which the use of a stereomicroscope is conceivable.

Advantages of the invention may include one or more of the following:

The access to the operating field is unobstructed;

The overall height of the microscope is decreased in an ergonomically advantageous manner; and An improved stereomicroscopy system for viewing an object or an intermediate image produced of the object which is particularly suitable for viewing an intermediate image with inverted image orientation and pseudo-stereoscopy.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A stereomicroscopy system for viewing at least one of an object and an intermediate image produced of an object, in microsurgery, comprising:

an objective system with an object plane for positioning at least one of the object and the intermediate image to be viewed;

a beam interchanging and image inverting system which supplies a first beam bundle directed to the left from the object plane in the direction of the objective system to the right of the objective system, and supplies a second beam bundle directed to the right from the object plane in the direction of the objective system to the left of the objective system, and inverts image orientations of the two beam bundles, wherein the beam interchanging and image inverting system comprises at least one Porro prism of the second kind.

2. The stereomicroscopy system according to claim 1, further comprising a separate Porro prism of the second kind for each one of the two beam bundles, wherein the two separate Porro prisms of the second kind are adjacent to each other to provide a symmetrical configuration.

3. The stereomicroscopy system according to claim 1, further comprising a first and a second ocular system for a first viewer to which the beam bundles supplied to the objective system on the left and on the right are supplied; further comprising a third and a fourth ocular system for a second viewer to which beam bundles supplied to the objective system on the top and the bottom are supplied; further comprising a first Porro prism of the second kind which supplies the beam bundles supplied on the left and right of the objective system and one of the beam bundles supplied to the objective system on the top and the bottom; and further comprising a second Porro prism of the second kind for supplying the other one of the beam bundles supplied to the objective system on the top and the bottom.

4. The stereomicroscopy system according to one of claims 1 to 3, wherein the beam interchanging and image inverting system is capable of being pivoted or shifted into the beam path.

5. The stereomicroscopy system according to claim 4, further comprising an ophthalmoscopic attachment for producing an intermediate image of an eye fundus in the object plane of the objective system, said ophthalmoscopic attachment being capable of being pivoted or inserted into the beam path together with the beam interchanging and image inverting system.

6. The stereomicroscopy system according to claim 4, wherein the beam interchanging and image inverting system is removable from the beam path in front of the objective system; wherein when the beam interchanging and image inverting system is positioned in the beam path, the object plane of the objective system is spaced apart from the objective system by a third distance; wherein, when the beam interchanging and image inverting system is removed from the beam path, the object plane is spaced apart from the objective system by a fourth distance; and wherein a difference between the third and the fourth distance has a predetermined value.

7. The stereomicroscopy system according to one of claims 1 to 3, further comprising an ophthalmoscopic lens system, said ophthalmoscopic lens system being insertable in front of the objective system for producing a laterally and horizontally inverted intermediate image of an eye fundus in the object plane of the objective system; further comprising an attachment lens system; wherein the beam interchanging and image inverting system and the attachment lens system are removable from the beam path in front of the objective system; and wherein geometric dimensions and optical media of the beam interchanging and image inverting system and focal lengths of the attachment lens system are adjusted such that, when the beam interchanging and image inverting system and the attachment lens system are positioned in the beam path, the intermediate image of the eye fundus can be positioned in the object plane of the objective system, the objective system being spaced apart from the eye by a first distance, and, when the beam interchanging and image inverting system and the attachment system are removed from the beam path, the cornea of the eye can be positioned in the object plane of the objective system, the objective system being spaced apart from the eye by a second distance, wherein the first distance and the second distance are substantially equal.

8. The stereomicroscopy system according to one of claims 1 to 3, wherein the beam interchanging and image inverting system is removable from the beam path in front of the objective system; wherein when the beam interchanging and image inverting system is positioned in the beam path, the object plane of the objective system is spaced apart from the objective system by a third distance; wherein, when the beam interchanging and image inverting system is removed from the beam path, the object plane is spaced apart from the objective system by a fourth distance; and wherein a difference between the third and the fourth distance has a predetermined value.

9. The stereomicroscopy system according to claim 8, wherein the difference between the third and the fourth distance is of from about 15 mm to about 40 mm.

10. The stereomicroscopy system according to claim 8, wherein the difference between the third and the fourth distance is of from about 20 mm to about 30 mm.

11. The stereomicroscopy system according to claim 8, wherein the difference between the third and the fourth distance is of from about 24 mm to about 26 mm.

12. A stereomicroscopy system for viewing an object or an intermediate image produced of an object, in particular in microsurgery, comprising:

an objective system with an object plane for positioning the object or intermediate image to be viewed, a left ocular system and a right ocular system; and a beam interchanging and image inverting system which supplies a first beam bundle entering the objective system on the left to the right ocular system and a second beam bundle entering the ocular system on the right to the left ocular system and inverts image orientations of the two beam bundles;

wherein the beam interchanging and image inverting system comprises a pair of shortened Porro prisms of the second kind.

13. The stereomicroscopy system according to claim 12, further comprising a magnification changing system disposed between the objective system and the two ocular systems, wherein the beam interchanging and image inverting system is disposed between the objective system and the magnification changing system.

14. The stereomicroscopy system according to claim 12 or 13, further comprising an attachment lens system insertable in front of the objective system for producing a vertically and horizontally inverted intermediate image of an object to be viewed in the object plane of the objective system.

15. A stereomicroscopy system for viewing an object or an intermediate image produced of an object, in microsurgery, comprising:

an objective system with an object plane for positioning the object or intermediate object to be viewed;

a left ocular system, to which a first beam bundle is supplied which enters the objective system on the left; and a right ocular system, to which a second beam bundle is supplied which enters the objective system on the right; and a beam interchanging system in the beam paths of the left and right ocular systems, said beam interchanging system reflects the first beam bundle supplied to the left ocular system into the right ocular system and for reflecting the second beam bundle supplied to the right ocular system into the left ocular system;

wherein the first and second beam bundles supplied to the beam interchanging system and the first and second beam bundles emerging from the beam interchanging system have the same image orientations.

16. The stereomicroscopy system according to claim 15, wherein the left ocular system and the right ocular system further comprise a portion with a convergent beam path, and wherein the beam interchanging system is disposed in the convergent beam path.

17. The stereomicroscopy system according to claims 15 or 16, wherein the beam interchanging system provides substantially the same optical path lengths for each of the second beam bundle supplied to the right ocular system and for the first beam bundle supplied to the left ocular system.

18. The stereomicroscopy system according to claim 17, further comprising an adjustment device for adjusting the optical path lengths of at least one of the first and second beam bundles.

19. The stereomicroscopy system according to claim 15 or 16, wherein the beam interchanging system is removable from the beam paths of the ocular systems, and further comprising an image inverting system, wherein said image inverting system being insertable into at least one of the beam paths of the ocular systems which image inverting system is adapted to invert the image orientation of the first and second beam bundles supplied to the left and the right ocular systems, respectively.

20. The stereomicroscopy system according to claim 19, wherein the beam interchanging system and the image inverting system provide substantially the same ocular intermediate image positions for the first and second beam bundles supplied to the ocular systems.

21. The stereomicroscopy system according to claim 15 or 16, further comprising an attachment lens system insertable in front of the objective system for producing a vertically and horizontally inverted intermediate image of an object to be viewed in the object plane of the objective system.

22. The stereomicroscopy system according to claim 15 or 16, wherein the beam interchanging system comprises:

a first mirror for deflecting the first beam bundle supplied to the ocular systems in a direction transverse to the direction of incidence into the beam interchanging system;

a second mirror for deflecting said deflected first beam bundle in a direction parallel to the direction of incidence;

a third mirror for deflecting said deflected first beam bundle in a direction opposite to the direction after the deflection at the first mirror;

a fourth mirror for deflecting said deflected first beam bundle towards and coaxially to the second beam bundle;

a fifth mirror for deflecting the second beam bundle in a direction transverse to the direction of incidence into the beam interchanging system;

a sixth mirror for deflecting said deflected second beam bundle in a direction opposite to the direction of incidence;

a seventh mirror for deflecting said deflected second beam bundle in a direction opposite to the direction after deflection at the fifth mirror; and an eighth mirror for deflecting said deflected second beam bundle towards and coaxially to the first beam bundle.

* * * * *

UNITED STATES PATENT AND TRADEMARK OFFICE
CERTIFICATE OF CORRECTION

PATENT NO.    : 6,598,972 B2
DATED         : July 29, 2003
INVENTOR(S)   : Fritz Strähle It is certified that error appears in the above-identified patent and that said Letters Patent is hereby corrected as shown below:

<u>Title page,</u>
Item [12], should read -- Strähle --.
Item [75], Inventor name should read -- Fritz Strähle --.
Item [73], Assignee should read -- Carl Zeiss-Stiftung trading as Carl Zeiss(DE) --.

Signed and Sealed this

Sixth Day of April, 2004

JON W. DUDAS
*Acting Director of the United States Patent and Trademark Office*